United States Patent [19]

Landeck et al.

[11] Patent Number: 4,810,267
[45] Date of Patent: * Mar. 7, 1989

[54] SCRUBBING OF GAS TO RECOVER LIGHT HYDROCARBONS

[75] Inventors: Heiner Landeck, Munich; Gerhard Ranke, Pöcking, both of Fed. Rep. of Germany

[73] Assignee: Linde Aktiengesellschaft, Wiesbaden, Fed. Rep. of Germany

[*] Notice: The portion of the term of this patent subsequent to Jan. 10, 2006 has been disclaimed.

[21] Appl. No.: 871,988

[22] Filed: Jun. 9, 1986

[30] Foreign Application Priority Data

Aug. 14, 1985 [DE] Fed. Rep. of Germany ....... 3529216
Oct. 7, 1985 [DE] Fed. Rep. of Germany ....... 3535764

[51] Int. Cl.$^4$ ............................................. B01D 19/00
[52] U.S. Cl. .......................................... 55/73; 55/48; 55/68
[58] Field of Search ................. 55/64, 84, 88, 37, 38, 55/40–48, 68–73

[56] References Cited

U.S. PATENT DOCUMENTS

| | | |
|---|---|---|
| 2,187,631 | 1/1940 | Schutt . |
| 2,223,197 | 11/1940 | Wirth ................................... 55/48 |
| 2,282,549 | 5/1942 | Sullivan, Jr. . |
| 2,335,855 | 12/1943 | Hall ..................................... 55/48 |
| 2,437,288 | 3/1948 | Anderson . |
| 2,455,803 | 12/1948 | Pierotti . |
| 2,570,066 | 10/1951 | Morrow et al. . |
| 2,685,941 | 8/1954 | Kassel .................................. 55/48 |
| 3,099,619 | 7/1963 | Harper . |
| 3,233,388 | 2/1966 | Karwat et al. ...................... 55/44 |
| 3,349,145 | 10/1967 | Uitti .................................... 260/672 |
| 4,072,604 | 2/1978 | Ward . |
| 4,102,983 | 7/1978 | Yamase et al. ..................... 55/88 |
| 4,460,384 | 7/1984 | Hirai et al. . |

FOREIGN PATENT DOCUMENTS

| | | |
|---|---|---|
| 936650 | 12/1955 | Fed. Rep. of Germany . |
| 1115786 | 9/1984 | U.S.S.R. .............................. 55/84 |
| 830972 | 3/1960 | United Kingdom ................ 55/43 |

Primary Examiner—Bernard Nozick
Attorney, Agent, or Firm—Millen & White

[57] ABSTRACT

For scrubbing $C_{2+}$ or $C_{3+}$ hydrocarbons from gaseous mixture containing hydrocarbons and/or inerts like $H_2N_2$, CO and possibly acid gases, e.g. $CO_2H_2S$, COS e.g. natural gas and the like, the scrubbing medium consists essentially of compounds having one to two rings formed by 5 or 6 carbon atoms, wherein the compounds comprise, in total, at least 9 and at most 17 carbon atoms, and the rings are saturated unsaturated or partially saturated especially alkylated ring compounds of 9 or 10 carbon atoms, e.g. isomeric forms of trimethylbenzene, propylbenzene, propylcyclohexane, tetrahydronaphthalene, decahydronaphthalene.

29 Claims, 2 Drawing Sheets

SCRUBBING OF GAS TO RECOVER LIGHT HYDROCARBONS

CROSS-REFERENCE TO RELATED APPLICATIONS

This application is related to copending and commonly assigned application entitled, "Scrubbing of Gas to Recover Light Hydrocarbons", Ser. No. 896,371.

BACKGROUND OF THE INVENTION

The present invention relates to gas absorption wherein light hydrocarbons are scrubbed from gaseous mixtures with a physical scrubbing agent.

It is conventional to separate $C_{2+}$ hydrocarbons from gaseous mixtures, such as natural gas, by the so-called Expander process. In this process, the precooled gas, after separation of condensate, is isentropically expanded in an expansion turbine. During this step, the cooling requirements for the condensation of $C_{2+}$ hydrocarbons from the gaseous mixture are satisfied at least in part by the cold-producing expansion of the gas.

However, if unfavorable marginal conditions occur, such as, for example, low concentrations of $C_{2+}$ hydrocarbons or simultaneously a higher content of $CO_2$ in the crude gas, then, alternatively, physical scrubbing procedures are also suitable for recovering the $C_{2+}$ fraction. Examples of known scrubbing media for such scrubbing operations are various polyethylene glycol dialkyl ethers (PGE), N-methylpyrrolidone (NMP), dimethylformamide (DMF), propylene carbonate, or sulfolane. Disadvantageous to the use of these known scrubbing media is that, besides the hydrocarbons, sour gases (e.g. $CO_2$, $H_2S$, COS) are likewise dissolved with relative ease, which gases are in most cases present in the crude gas. At the same time the solubility of $C_{2+}$ hydrocarbons is very low. Under practical conditions, this means that, besides $C_{2+}$ hydrocarbons, a considerable portion of the $CO_2$ present in the gas is also scrubbed out and the amount of the circulated solvent is relatively large. In order to produce a $C_{2+}$-fraction suitable for further processing, two different ways for the recovery of this fraction from the loaded solvent are possible. The first way, normally used in oil scrubbing systems, was distillation, thereby separating the solvent as bottoms product and the absorbed gases as the overhead stream. Thereafter, this overhead stream had to be separated into a $C_{2+}$-fraction and a gas containing $CO_2$, $CH_4$ and lighter components like inert gases such as $H_2$, $N_2$ and CO. The second way is the expansion of the loaded solvent to low pressure. The flash gas is compressed and fed to a rectification column for the further recovery and purification of the $C_{2+}$ product. In the rectification of the desorbed gas into methane as the overhead product and residual $C_{2+}$ hydrocarbons as the bottoms product, problems are also encountered due to the tendency to form an azeotrope between $CO_2$ and ethane.

SUMMARY OF THE INVENTION

An object of this invention is to provide an improved scrubbing medium for removing light hydrocarbons, especially $C_{2+}$ or $C_{3+}$ hydrocarbons, from gaseous mixtures.

Upon further study of the specification and appended claims, further objects and advantages of this invention will become apparent to those skilled in the art.

To attain these objects, there are employed as the scrubbing media: compounds having one or two rings formed by 5 or 6 carbon atoms, respectively, wherein the compounds, in total, contain at least 9 and at most 17 carbon atoms, and the rings are saturated, unsaturated, or partially saturated. Consequently, the optimum scrubbing medium is constituted by an organic ring compound with 5 or 6 carbon atoms in the ring and, in total, between 9 and 17 carbon atoms wherein the ring(s) can have aliphatic, olefinic or aromatic character. The fusion of several rings is possible in this connection, but it is preferred that the melting point of the compound be below 0° C. and the boiling point be above 130° C., especially from 130° C. to 250° C.

The compounds utilized according to this invention exhibit, besides stability, other excellent properties rendering them particularly suitable for use as scrubbing media for $C_{2+}$ or $C_{3+}$ hydrocarbons. The compounds are highly selective between ethane/propane on the one hand, and the light components in the crude gas on the other hand, such as, for example, methane $N_2$, $H_2$ and CO. Also, the absolute solubility of ethane/propane in the compounds is relatively high. The compounds to be used according to this invention exhibit a $C_2$ or $C_3$ solubility which in particular, is higher than that of $CO_2$. Accordingly, the $CO_2$ can remain at least in part in the scrubbed gas. Moreover, the vapor pressure of the compounds employed is so low, so that losses of scrubbing medium are minor, and at the same time satisfactory purities of the resultant products can be realized. All of the aforementioned advantageous properties of the compounds to be utilized as scrubbing agents according to this invention have not been simultaneously associated with the organic liquids heretofore suggested as scrubbing media for the scrubbing of natural gas and the like.

According to a preferred embodiment of the process of this invention, compounds to be employed as scrubbing media have the formulae I

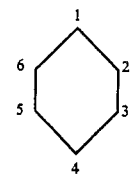

A

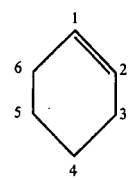

B

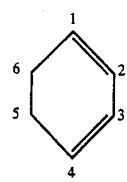

C

-continued

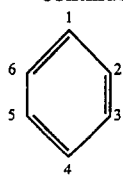

wherein in the positions 1 to 6 there may be one or two substituted groups, being identical or different, representing a hydrogen atom or an alkyl radical of 1–5 carbon atoms. Accordingly, examples for suitable scrubbing media, include, but are not limited to alkylated ring-compounds of 9 or 10 carbon atoms. These relatively heavy ring compounds exhibit a very high selectivity between ethane/propane and methane and a high solubility of ethane/propane.

Accordingly, the following compounds are particularly suitable as scrubbing media:

Formula I A:
Isomeric forms of trimethylcyclohexane, propylcyclohexane, butylcyclohexane, all forms having a saturated ring;

Formula I B:
Isomeric forms of trimethylcyclohexene, especially tetrahydromesitylene, butylcyclohexene, propylcyclohexene, all forms having a partially saturated ring;

Formula I C:
Isomeric forms of trimethylcyclohexadiene, butylcyclohexadiene, propylcyclohexadiene, all forms having a partially saturated ring;

Formula I D:
Isomeric forms of methylethylbenzene, trimethylbenzene, butylbenzene, propylbenzene, methylpropylbenzene, diethylbenzene, dimethylethylbenzene, tetramethylbenzene, all forms having an unsaturated ring;

All isomeric forms of trimethylbenzene or propylbenzene are utilized herein as the especially preferred scrubbing media.

Likewise, the scrubbing agents of this invention also include, but are not limited to the following groups of compounds and particular species thereof.

Compounds to be employed as scrubbing medium have the formulae II

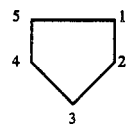

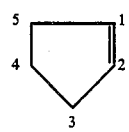

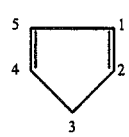

wherein in the positions 1 to 5 there may be one or two substituted groups, being identical or different, representing a hydrogen atom or an alkyl radical of 1–5 carbon atoms.

Accordingly, the following compounds are particularly suitable as scrubbing media.

Formula II A:
Isomeric forms of diethylcyclopentane, tetramethylcyclopentane, butylcyclopentane, all forms having a saturated ring;

Formula II B:
Isomeric forms of pentylcyclopentene, all forms having a partially saturated ring;

Formula II C:
Isomeric forms of methylpropylcyclopentadiene, all forms having an unsaturated ring.

Further compounds to be employed as scrubbing media have the formulae III

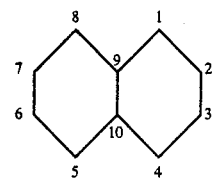

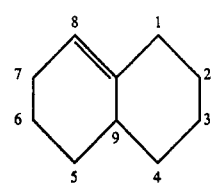

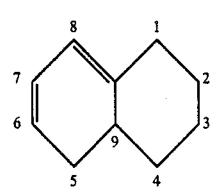

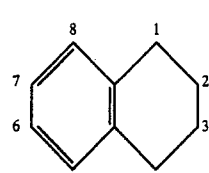

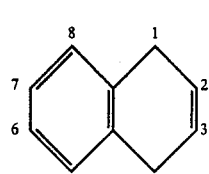

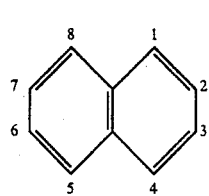

wherein in the positions 1 to 8, 9 or 10 there may be one or two substituted groups, being identical or different, representing a hydrogen atom or an alkyl radical of 1 to 5 carbon atoms.

Accordingly, the following compounds are particularly suitable as scrubbing media:
Formula III A:
decahydronaphthalene (decaline). (saturated rings)
Formula III B:
Isomeric forms of bicyclodecene
Formula III C:
Isomeric forms of bicyclodecadiene
Formula III D:
1,2,3,4-tetrahydronaphthalene (tetraline)
Formula III E:
Isomeric forms of dihydronaphthalene
Formual III F:
1-methylnaphthalene. (unsaturated rings)

Further compounds to be employed as scrubbing media have the formulae IV

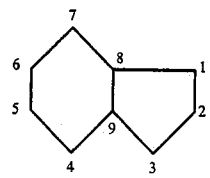
A

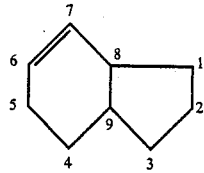
B

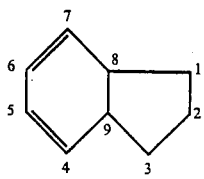
C

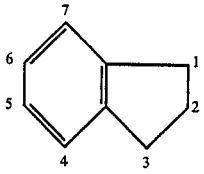
D

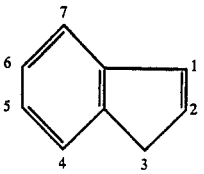
E

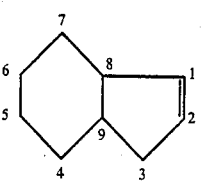
F wherein in the positions 1 to 7 or 9 there may be one or two substituted groups, being identical or different, representing a hydrogen atom or an alkyl radical of 1 to 5 carbon atoms.

Accordingly, the following compounds are particularly suitable as scrubbing media:
Formula IV A:
hydrindane
Formula IV B:
Isomeric forms of tetrahydroindane
Formula IV C:
Isomeric forms of bicyclononadiene
Formula IV D:
indane (hydrindene)
Formula IV E:
Isomeric forms of indene
Formula IV F:
Isomeric forms of hexahydroindene.

Further compounds to be employed as scrubbing media have the formulae V

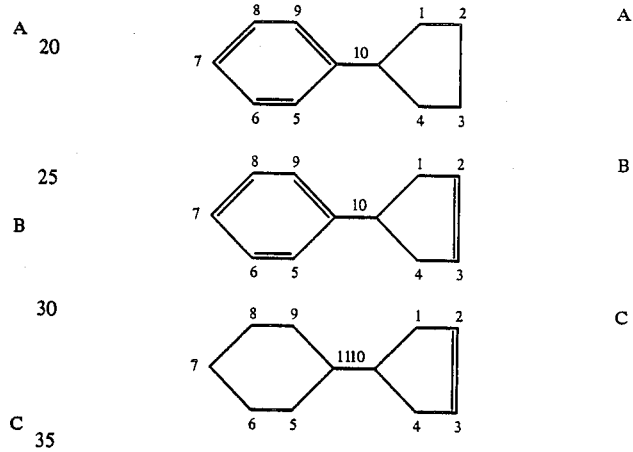

wherein in the positions 1 to 9, 10 or 11 there may be one or two substituted groups, being identical or different, representing a hydrogen atom or an alkyl radical of 1 to 5 carbon atoms.

Accordingly, the following compounds are particular suitable as scrubbing media:
Formula V A:
cyclopentylbenzene
Formula V B:
Isomeric forms of phenylcyclopentene
Formula V C:
Isomeric forms of cyclohexylcyclopentene.

Further compounds to be employed as scrubbing media have the formulae VI

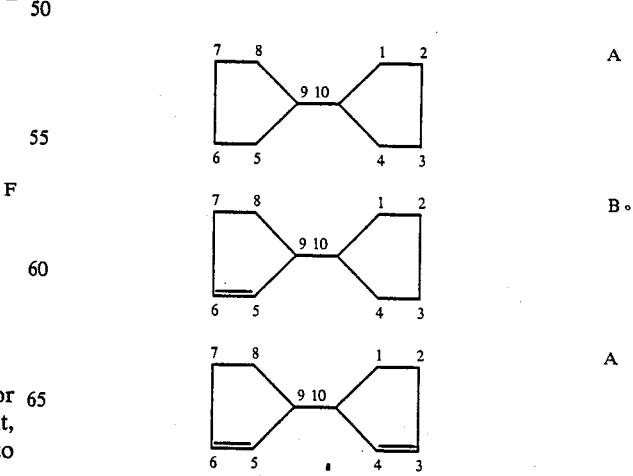

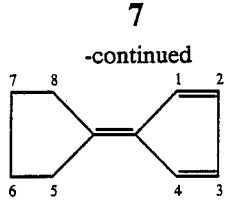

wherein in the positions 1 to 8 or 10 there may be one or two substituted groups, being identical or different, representing a hydrogen atom or an alkyl radical of 1 to 5 carbon atoms.

Accordingly, the following compounds are particularly suitable as scrubbing media:

Formula VI A:
bicyclopentyl
Formula VI B:
Isomeric forms of cyclopentencyclopentyl
Formula VI C:
Isomeric forms of bicyclopentenyl
Formula VI D:
cyclopentylidene-cyclopentadiene.

According to a further development of the idea of this invention, the provision is made to use as the scrubbing media also halogen-substituted compounds. In particular, the compounds can be chlorine-substituted. For example, 1-chloronaphthalene.

It is also contemplated in this invention that the compounds can be modified by the substitution, addition or interposition of other atoms which do not materially affect the basic and novel aspects to this invention, and such modified compounds are embraced herein.

The compounds herein can be utilized in the pure form as well as in a mixture with one another.

In addition to the use of these compounds, it is also possible to use as the scrubbing agent, mixtures of said compounds with solvents such as benzene, toluene or xylene, or polar, organic, water-soluble physical solvents. In particular, those added solvents suitable for this invention are those conventionally employed for sour gas scrubbing operations, such as alcohols, ketones, ethers, polyethers, amides, esters. Typical solvents for physical absorption methods for removal of sour gas are cited, for example, in A. L. Kohl, F. C. Riesenfeld, "Gas Purification" 3rd edition, 1979; as well as R. N. Maddox, "Gas Conditioning and Processing" vol. 4, 1982, incorporated by reference herein.

By the addition of toluene or xylene, the viscosity of the scrubbing medium is lowered. Moreover, the ring character of the scrubbing medium is enhanced, and these additives are also selective in favor of ethane/propane as compared to $CO_2$.

The additives are admixed to the compounds of this invention in such amounts that do not completely mask the benefits of this invention which would in turn materially alter the basic and novel characteristics of this invention. Thus, the scrubbing agent will preferably consist essentially of the above described ring compounds of this invention containing 9-17 carbon atoms, with 5 or 6 atoms in a ring. In any case, the added solvents are preferably used in monor amounts, advantageously up to 25% by weight, and preferably in the range of 3 to 20% by weight relative to the weight of the compounds of this invention. With such low amounts of sour gas solvents being added, the $CO_2$ solubility in the scrubbing medium is slightly increased, but on the other hand, water can also be scrubbed out of the crude gas to such an extent that the drying of crude gas can in some cases be advantageously omitted.

The addition of water dissolving solvents to the recommended solvents is especially preferred in those cases, where a low concentration of $C_{2+}$ or $C_{3+}$ is present in the feed gas. In these cases, the methane rich gas can be dried at least to a water dewpoint suitable for pipeline transportation (usually 7 lbs $H_2O$ per MMSCF) and only the small part of the absorbed gas, which has to be handled in the distillation column has to be dried. Without the addition of the water dissolving solvent, the entire feed gas must be dried by absorbers or a glycol wash. It is known to use water dissolving additives with special solvents, e.g., methanol as additive to toluene for selective sulfur removal or to N-methylpyrrolidone, if $C_2H_2$ is removed. In the special case of recovery of heavier hydrocarbons, the additive must have a much higher boiling point than methanol. Preferred additions are therefore polyethyleneglycoldialkyl ethers or similar components with a high boiling temperature, e.g. NMP.

The scrubbing step is advantageously performed at temperatures of between $-20°$ and $+40°$ C. The pressure at which scrubbing takes place is not significant so that the gaseous mixture can be treated at crude gas pressure.

Especially preferred scrubbing media consist essentially of trimethylbenzene and, in this connection, particularly 1,2,4-trimethylbenzene (pseudocumene) or 1,3,5-trimethylbenzene (mesitylene) and propylbenzene, in particular n-propylbenzene, decaline, or tetraline.

The loaded scrubbing medium is preferably recirculated by any conventional regeneration technique, e.g. thermal, pressure reduction and/or stripping, with the preferred technique being pressure reduction and compression of the flashgas.

The raw gases that are especially advantageously treated by this invention comprise natural gas and all associated oil gases, but also gases from refinery or gases produced by gasification of coal or another organic feedstock.

Tables 1 to 4, respectively, set forth below, indicate the absolute solubilities for $C_2H_6$ and $C_3H_8$ and selectivities for $C_2H_6$ and $C_3H_8$ with respect to $CH_4$ and for $C_2H_6$ and $C_3H_8$ with respect to $CO_2$ at 20° C. for several conventional scrubbing media (Tables 1 and 3) and scrubbing media according to this invention (Tables 2 and 4). In this context, $\lambda$ indicates the technical solubility coefficient in $Nm^3$/ton. ata, (cubic meters under standard conditions per ton of scrubbing medium and per atmosphere partial pressure at a given temperature).

TABLE 1

| Scrubbing Medium | $\lambda C_2H_6$ | $\lambda C_2H_6:\lambda CH_4$ | $\lambda C_2H_6:\lambda CO_2$ |
| --- | --- | --- | --- |
| Polyethylenglycol dialkyl ether | 1.7 | 6.3 | 0.52 |
| NMP | 1.2 | 5.2 | 0.30 |
| DMF | 1.3 | 4.6 | 0.26 |
| Propylene carbonate | 1.0 | 5.0 | 0.34 |

TABLE 2

| Scrubbing Medium | $\lambda C_2H_6$ | $\lambda C_2H_6:\lambda CH_4$ | $\lambda C_2H_6:\lambda CO_2$ |
| --- | --- | --- | --- |
| Trimethylbenzene | 4.1 | 6.3 | 1.7 |
| Propylbenzene | 4.3 | 7.0 | 1.7 |
| Propylcyclohexane | 5.1 | 6.9 | 2.2 |
| Decahydronaphthalene | 3.9 | 8.0 | 3.1 |

TABLE 2-continued

| Scrubbing Medium | $\lambda C_2H_6$ | $\lambda C_2H_6{:}\lambda CH_4$ | $\lambda C_2H_6{:}\lambda CO_2$ |
|---|---|---|---|
| (Decaline) Tetrahydronaphthalene (Tetraline) | 2.7 | 8.4 | 1.9 |

TABLE 3

| Scrubbing Medium | $\lambda C_3H_8$ | $\dfrac{\lambda C_3H_8}{\lambda CH_4}$ | $\dfrac{\lambda C_3H_8}{\lambda C_2H_6}$ | $\dfrac{\lambda C_3H_8}{\lambda CO_2}$ |
|---|---|---|---|---|
| Polyethylen glycol dialkyl ether | 5.4 | 20.0 | 3.2 | 1.6 |
| NMP | 3.8 | 16.5 | 3.2 | 0.94 |
| DMF | 5.3 | 18.9 | 4.0 | 1.1 |
| Propylene carbonate | 2.3 | 11.0 | 2.3 | 0.79 |

TABLE 4

| Scrubbing medium | $\lambda C_3H_8$ | $\dfrac{\lambda C_3H_8}{\lambda CH_4}$ | $\dfrac{\lambda C_3H_8}{\lambda C_2H_6}$ | $\dfrac{\lambda C_3H_8}{\lambda CO_2}$ |
|---|---|---|---|---|
| Trimethylbenzene | 15.8 | 24.3 | 3.9 | 6.4 |
| Propylbenzene | 16.2 | 26.6 | 3.8 | 6.3 |
| Propylcyclohexane | 17.4 | 23.8 | 3.4 | 7.4 |
| Decaline | 16.2 | 33.1 | 4.1 | 12.9 |
| Tetraline | 11.1 | 34.7 | 4.2 | 7.8 |

As can be seen from the tables, absolute $C_2H_6$ and $C_3H_8$ solubility as well as selectivity are more favorable for the compound of this invention than for those scrubbing media proposed heretofore.

Since the amount of scrubbing medium circulated in a physical scrubbing operation is inversely proportional to the solubility of the key component in the gas to be scrubbed, and the dissolved amount of $CH_4$ and/or $CO_2$ and lighter gases is proportional to the quantity of scrubbing medium and the solubility of $CH_4$ and $CO_2$ and lighter gases it can be seen that, in the present instance, the pumping energy as well as the compression energy for compressing the methane and/or $CO_2$ and lighter gases, dissolved in the scrubbing column are both lower, when using the compounds of this invention, e.g., trimethylbenzene, than in the case of the conventional solvents.

Without further elaboration, it is believed that one skilled in the art can, using the preceding description, utilize the present invention to its fullest extent. The following specific embodiment is, therefore, to be construed as merely illustrative for the comparison of different solvents, and not limitative of the remainder of the disclosure in any way whatsover.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts, and wherein.

DESCRIPTION OF THE DRAWINGS

Figure 1:
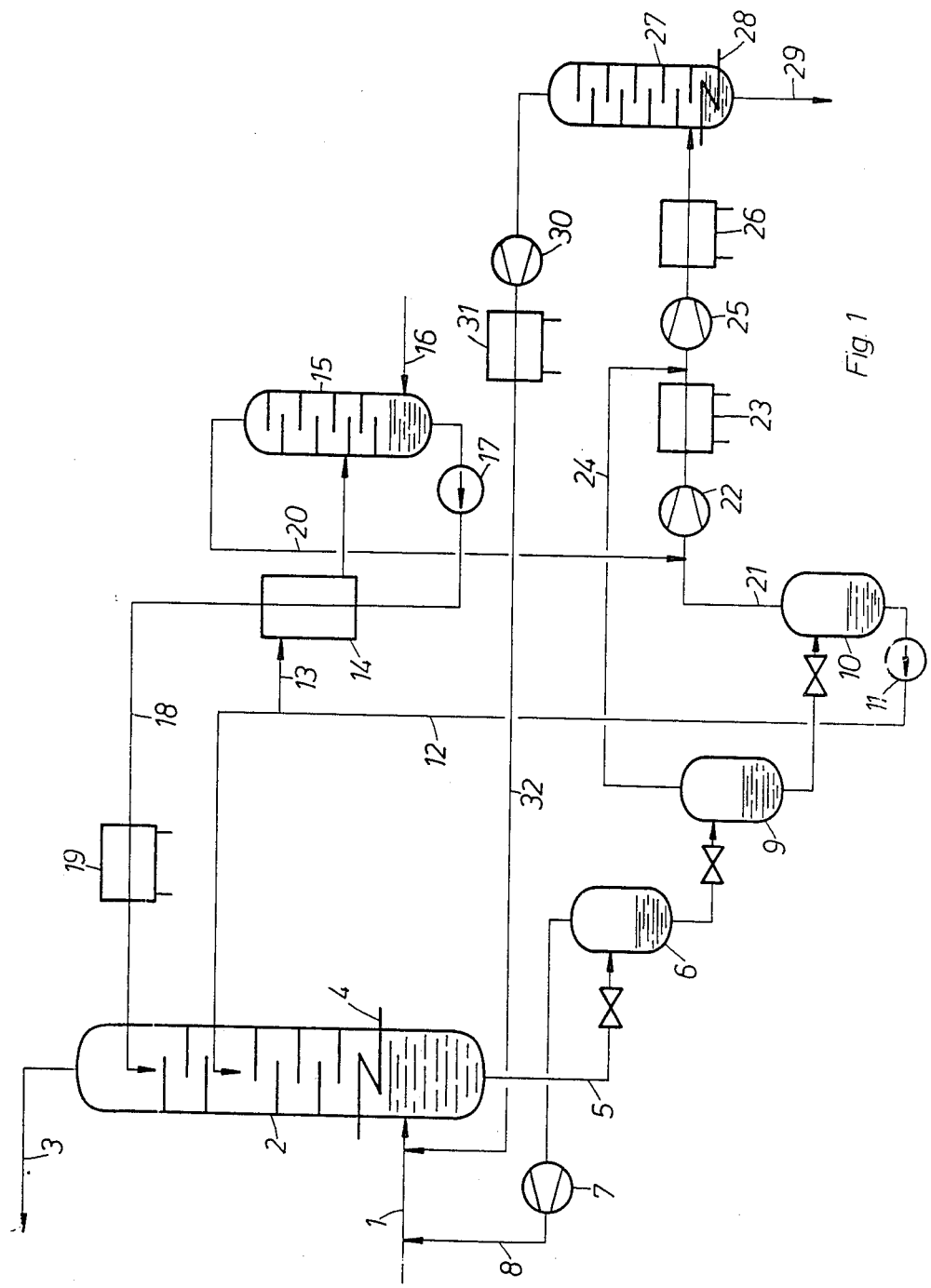
FIG. 1 shows a schematic flow diagram for the recovery of $C_{2+}$ hydrocarbons and FIG. 2 shows a schematic flow diagram for the recovery of $C_{3+}$ hydrocarbons.

FIG. 1: Feed gas is passed under pressure via conduit 1 into scrubbing column 2, where it is scrubbed with a scrubbing medium which solves $C_{2+}$ hydrocarbons. The scrubbed gas, comprising methane and nitrogen, leaves the column via conduit 3. In order to keep a constant temperature on the bottom of column 2, the heat of absorption, which is not compensated by temperature increase of the solvent, is removed by a refrigerant in cooling coil 4.

The loaded scrubbing medium is withdrawn from the bottom of column 2 via conduit 5 and flashed into separator 6. The flash gas from separator 6 is recompressed in compressor 7 and recycled to the feed gas via conduit 8. The partially deflashed scrubbing medium from separator 6 is flashed into a second separator 9, the bottoms of which is flashed into a third separator 10. The pressure of the bottoms of separator 10 is raised by means of pump 11, which conveys the scrubbing medium to column 2 via conduit 12. A part of the scrubbing medium is branched off through conduit 13, heated in heat exchanger 14 and fed into solvent stripper 15. There the scrubbing medium is treated with a scrubbing gas introduced via conduit 16. The bottoms of stripper 15 is pressurized by means of pump 17, cooled in 14 and fed to column 2 via conduit 18 and cooler 19.

Via conduit 20 the top fraction of solvent stripper 15 is conveyed to conduit 21 and combined with the flash gas from separator 10. Both streams are pressurized in compressor 22 and cooled in cooler 23. Then they are combined with flash gas from separator 9, brought over via conduit 24. The combined streams are compressed in compressor 25, cooled in cooler 26 and fed into demethanizer 27, which is provided with a bottom heating 28. The bottoms of demethanizer 27, comprising all $C_{2+}$ hydrocarbons, are led off via conduit 29, while the top fraction, comprising lighter hydrocarbons and nitrogen, is pressurized in compressor 30, cooled in cooler 31 and recycled to the feed gas via conduit 32.

Figure 2:
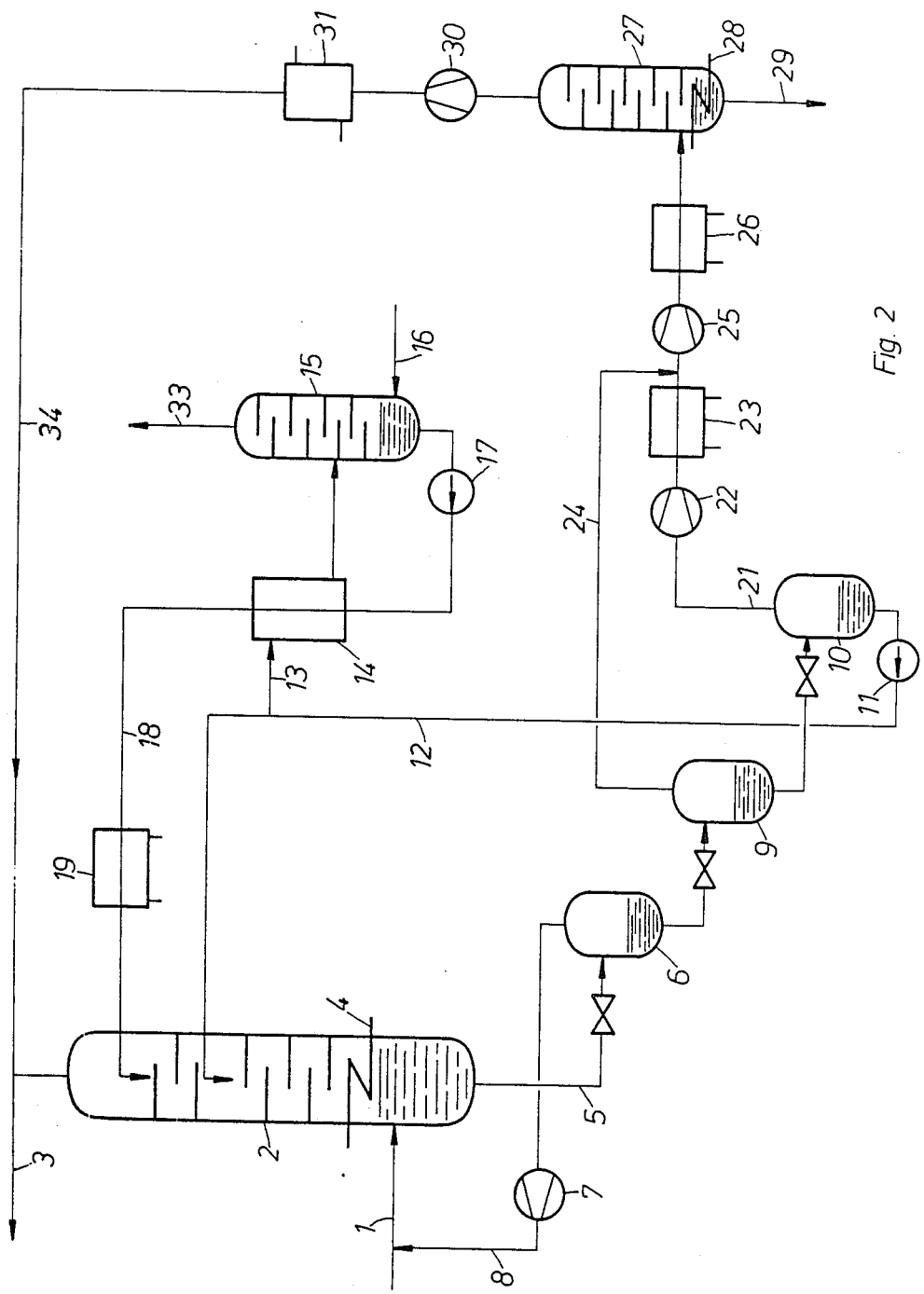

FIG. 2: In this embodiment of the invention a scrubbing plant is shown similar to that of FIG. 1. Therefore, comparable or like parts have been given same reference numerals as in FIG. 1. The main difference is that in the embodiment $C_{3+}$ hydrocarbons are scrubbed out of a $CO_2$ containing feed gas, while $C_1$ and $C_2$ hydrocarbons and $CO_2$ leave the plant via conduit 3. Further, the top fraction of solvent stripper 15, comprising some heavier hydrocarbons and $CO_2$, is drawn off via conduit 33 and not recycled to the flashgas. Last not least, column 27 does not act as demethanizer, but as deethanizer. So the bottoms fraction of deethanizer 27, drawn off via conduit 29, comprises $C_{3+}$ hydrocarbons, while the top fraction is not recycled to the feed gas, but conveyed via conduit 34 with compressor 30 and cooler 31 and combined with the product gas in conduit 3.

In the following table 5 physical parameters are put together which are fixed for all scrubbing media, while the other data are given by process calculation.

TABLE 5

| | FIG. 1 | | FIG. 2 | |
|---|---|---|---|---|
| Reference numeral | temperature °C. | pressure bar | temperature °C. | pressure bar |
| 1 | 20 | 34.5 | 20 | 70 |
| 2 (bottom) | 20 | 34.5 | | 70 |
| 6 | | 18 | | 25 |
| 9 | | 3.1 | | 9 |
| 10 | | 1.034 | | 1.23 |
| 23 (end) | 20 | 3.1 | 45 | 1.0 |
| 26 (end) | 20 | 25.8 | 45 | 26 |
| 27 | | 25.8 | 20 | 26 |
| 31 (end) | 20 | 34.5 | 20 | 70 |

In the following table 6 there are put together process data and consumption data for the recovery of $C_{2+}$ hydrocarbons with different scrubbing media from 1000 mol/sec feed gas of the following composition:

| | |
|---|---|
| $N_2$ | 1.68 mol % |
| $CH_4$ | 81.13 mol % |
| $C_2H_6$ | 8.71 mol % |
| $C_3H_8$ | 4.79 mol % |
| $C_4H_{10}$ | 2.41 mol % |
| $C_5H_{12}$ | 0.97 mol % |
| $C_6H_{14}$ | 0.31 mol %. |

TABLE 6

| | Mesitylene | Propylbenzene | Decaline | PGE |
|---|---|---|---|---|
| Amount of circulating scrubbing medium (tons/hour) | 627.6 | 592.8 | 649.4 | 1567.3 |
| Temperature (°C.), head of scrubbing column 2 | 23.4 | 23.3 | 23.7 | 25.5 |
| Flow to demethanizer (mol/sec) | 270.5 | 261.3 | 249.4 | 271.0 |
| Power consumption (kilowatt) | | | | |
| compression (gases) | 2625.8 | 2520.7 | 2394.0 | 2622.4 |
| pumping (liquids) | 898.2 | 872.7 | 955.1 | 1901.5 |
| separate cooling | 765.8 | 780.3 | 893.5 | 1631.2 |
| total (kilowatt) | 4289.8 | 4173.7 | 4232.6 | 6155.1 |

For comparison of the different scrubbing media a constant yield of 85% $C_2H_6$ based on the $C_2H_6$ in the feed gas was given by variation of the amount of scrubbing media.

In table 7 there are put together process data and consumption data for the recovery of $C_{3+}$ hydrocarbons with different scrubbing media from 1000 mol/sec feedgas of the following composition:

| | |
|---|---|
| $CO_2$ | 10 mol % |
| $CH_4$ | 80.8 mol % |
| $C_2H_6$ | 5.5 mol % |
| $C_3H_8$ | 2.2 mol % |
| $C_4H_{10}$ | 1.0 mol % |
| $C_5H_{12}$ | 0.3 mol % |
| $C_6H_{14}$ | 0.2 mol %. |

TABLE 7

| | Mesitylene | Propylbenzene | Decaline | PGE | NMP | DMF |
|---|---|---|---|---|---|---|
| Amount of circulating scrubbing medium (tons/hour) | 129.7 | 120.2 | 148.2 | 412.4 | 594.1 | 605.4 |
| Temperature (°C.), head of scrubbing column 2 | 24.3 | 24.0 | 26.5 | 24.2 | 25.3 | 27.5 |
| Flow from deethanizer (mol/sec) | 65.2 | 61.5 | 49.7 | 141.7 | 145.5 | 157.9 |
| Power consumption (kilowatt) | | | | | | |
| compression (gases) | 1198.0 | 1131.4 | 983.1 | 2297.1 | 2475.3 | 2627.6 |
| pumping (liquids) | 386.5 | 360.3 | 454.1 | 1046.1 | 1483.9 | 1660.9 |
| separate cooling | 212.6 | 208.5 | 264.3 | 782.0 | 1059.4 | 1222.3 |
| total | 1797.1 | 1700.2 | 1701.5 | 4125.1 | 5018.6 | 5510.8 |

PGE, NMP and DMF are known sour gas scrubbing media.

For comparison of the different scrubbing media a constant yield of 95% $C_3H_8$ based on the amount of $C_3H_8$ in the feedgas was given by variation of the amount of scrubbing media.

The preceding examples can be repeated with similar success by substituting the generically or specifically described solvents and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the recovery of:
   (a) $C_{2+}$ hydrocarbons or
   (b) $C_{3+}$ hydrocarbons from a gaseous mixture containing the hydrocarbons, $CO_2$ and at least one of $CH_4$ and inert gas from the group comprising $H_2$, $N_2$ and CO, said process comprising scrubbing said gaseous mixture with a scrubbing medium to remove selectively (a) or (b) by absorption and regenerating resultant loaded scrubbing medium to produce a product stream containing (a) or (b) and regenerated scrubbing medium, the improvement wherein the scrubbing medium comprises a compound having one to two rings each formed by 5 or 6 carbon atoms wherein the compound comprises in total at least 9 and at the most 17 carbon atoms, and the rings are saturated, unsaturated or partially saturated.

2. A process according to claim 1, said compounds being of the following formulas:

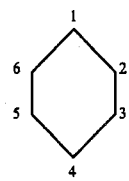

A

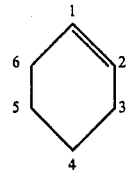

B

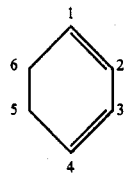

C

-continued

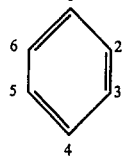

D wherein in the positions 1 to 6 there may be one or two substituted groups, being identical or different, representing a hydrogen atom or an alkyl radical of 1–5 carbon atoms.

3. A process according to claim 1 wherein the compound is an alkylated mononuclear ring of 9 or 10 carbon atoms in total.

4. A process according to claim 1, said compound being isomeric trimethylbenzenes or propylbenzenes.

5. A process according to claim 1, said compound being of the following formulas:

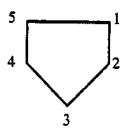

A

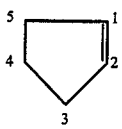

B

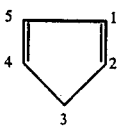

C wherein in the positions 1 to 5 there may be one or two substituted groups, being identical or different, representing a hydrogen atom or an alkyl radical of 1–5 carbon atoms.

6. A process according to claim 1, said compound being trimethylcyclohexane, propylcyclohexane, or butylcyclohexane.

7. A process according to claim 1, said compound being butylcyclopentane.

8. A process according to claim 1, said compound being of the following formulas:

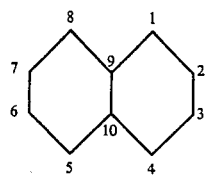

A

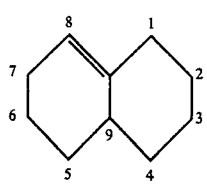

B

-continued

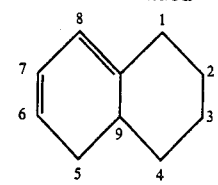

C

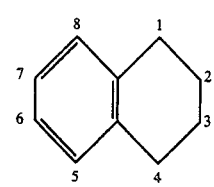

D

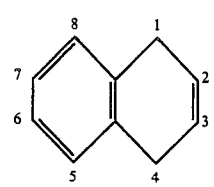

E

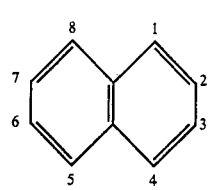

F wherein in the positions 1 to 8, 9 or 10 there may be one or two substituted groups, being identical or different, representing a hydrogen atom or an alkyl radical of 1 to 5 carbon atoms.

9. A process according to claim 1, said compounds being decahydronaphthalene, tetrahydronaphthalene, or 1-methylnaphthalene.

10. A process according to claim 1, said compound being of the following formulas:

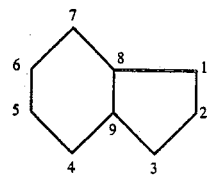

A

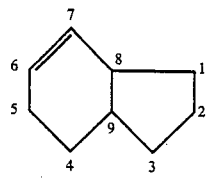

B

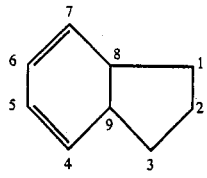

C

-continued

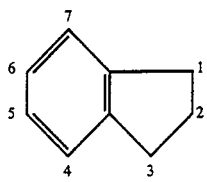 D

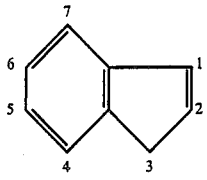 E

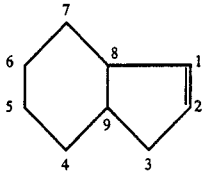 F wherein in the positions 1 to 7 or 9, there may be one or two substituted groups, being identical or different, representing a hydrogen atom or an alkyl radical of 1 to 5 carbon atoms.

11. A process according to claim 1, said compound being indan or indene.

12. A process according to claim 1, said compound being of the following formulas:

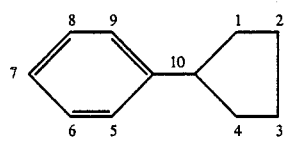 A

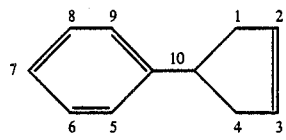 B

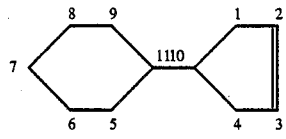 C wherein in the positions 1 to 9, 10 or 11 there may be one or two substituted groups, being identical or different, representing a hydrogen atom or an alkyl radical of 1 to 5 carbon atoms.

13. A process according to claim 1, said compound being of the following formulas:

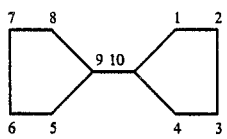 A

-continued

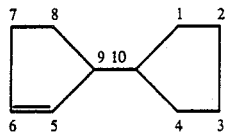 B

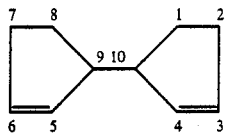 A

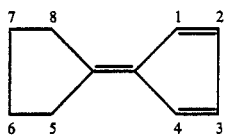 D wherein in the positions 1 to 8 or 10 there may be one or two substituted groups, being identical or different, representing a hydrogen atom or an alkyl radical of 1 to 5 carbon atoms.

14. A process according to claim 1, where the scrubbing medium comprises a mixture of at least two of said compounds.

15. A process according to claim 1, said scrubbing medium further comprising a minor amount of a polar, organic, water-dissolving, physical solvent.

16. A process according to claim 1, characterized by conducting the scrubbing operation at temperatures of between $-20°$ C. and $+40°$ C.

17. A process according to claim 1, said compound being halogen-substituted.

18. A process according to claim 17, said compound being chlorine-substituted.

19. A process according to claim 1, said scrubbing medium further comprising toluene or xylene.

20. A process according to claim 19, said scrubbing medium further comprising a minor amount of a polar, organic, water-dissolving, physical solvent.

21. A process according to claim 19, said toluene, or xylenes being present in an amount of up to 25% by weight of said compound.

22. A process according to claim 1, wherein said gaseous mixture contains methane and said scrubbing agent consists essentially of at least one alkylated ring compound of 9 or 10 carbon atoms.

23. A process according to claim 22, wherein the gaseous mixture contains a major amount of methane.

24. A process according to claim 22, said alkylated ring compound being admixed with toluene or xylene.

25. A process according to claim 22, said alkylated ring compound being admixed with a polar, organic, water-dissolving, physical solvent to remove $H_2O$ from the gas.

26. A process according to claim 22, wherein the alkylated ring compound is trimethylbenzene propylbenzene, decaline or tetraline.

27. A process according to claim 22, wherein the gaseous mixture further contains sulfur compounds.

28. A process according to claim 27, wherein the gaseous mixture contains a major amount of methane.

29. In a process for the recovery of:
    (a) $C_{2+}$ hydrocarbons, or
    (b) $C_{3+}$ hydrocarbons
from a gaseous mixture containing the hydrocarbons, methane, $CO_2$, sulfur compounds and at least one of $CH_4$ and inert gas from the group comprising $H_2$, $N_2$ and CO, said process comprising scrubbing said gaseous mixture with a scrubbing medium to remove selectively (a) or (b) by absorption and regenerating resultant loaded scrubbing medium to produce a product stream containing (a) or (b) and regenerated scrubbing medium, the improvement wherein the scrubbing medium comprises a compound having one to two rings formed by 5 or 6 carbon atoms, wherein a compound comprises in total at least 9 and at most 17 carbon atoms, and the rings are saturated, unsaturated or partially saturated.

* * * * *